US012414754B2

(12) United States Patent
Pulijala et al.

(10) Patent No.: US 12,414,754 B2
(45) Date of Patent: Sep. 16, 2025

(54) AUTO POSITIONING OF X-RAY TUBE SUPPORT WITH RESPECT TO DETECTOR

(71) Applicant: KONINKLIJKE PHILIPS N.V., Eindhoven (NL)

(72) Inventors: Sanjay Bharadwaj Pulijala, Pune (IN); Sirosh Mullan, Pune (IN); Harshad Mahajan, Pune (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 19/100,141

(22) PCT Filed: Jun. 9, 2023

(86) PCT No.: PCT/EP2023/065515
§ 371 (c)(1),
(2) Date: Jan. 31, 2025

(87) PCT Pub. No.: WO2024/027969
PCT Pub. Date: Feb. 8, 2024

(65) Prior Publication Data
US 2025/0255572 A1   Aug. 14, 2025

(30) Foreign Application Priority Data
Aug. 1, 2022   (EP) .................... 22188066

(51) Int. Cl.
*A61B 6/00*   (2024.01)
*A61B 6/58*   (2024.01)

(52) U.S. Cl.
CPC ............ *A61B 6/587* (2013.01); *A61B 6/4452* (2013.01); *A61B 6/4464* (2013.01); *A61B 6/547* (2013.01)

(58) Field of Classification Search
CPC . A61B 6/025; A61B 1/00112; A61B 1/00147; A61B 1/00163; A61B 1/042;
(Continued)

(56) References Cited

U.S. PATENT DOCUMENTS

2003/0043964 A1* 3/2003 Sorenson ............... G01N 23/04
378/58
2013/0127613 A1   5/2013 Zhang
(Continued)

FOREIGN PATENT DOCUMENTS

CN   114190957 A   3/2022
DE   102013219137 A1   3/2015
EP   3406196 A1   11/2018

OTHER PUBLICATIONS

PCT International Search Report, International application No. PCT/EP2023/065515, Sep. 15, 2023.

*Primary Examiner* — Don K Wong
(74) *Attorney, Agent, or Firm* — Larry Liberchuk (57) ABSTRACT

The present invention relates to medical imaging. In order to facilitate the alignment of an X-ray tube with respect to an X-ray detector, a positioning system (160) is provided for controlling an X-ray tube support system to align an X-ray tube with an X-ray detector. The positioning system comprises a radio frequency (RF) based localization system (170), an optical camera (180), and a controller (190). The RF-based localization system comprises a first RF device (172) that is attachable to the X-ray detector, and a plurality of second RF devices (174, 176, 178) that are arranged in a known geometric relationship to the X-ray tube (112) and configured to use an RF signal to localize the first RF device so as to provide first position information of the X-ray detector. The controller is configured to generate, based on the first position information of the X-ray detector, a first control signal that is usable for controlling the X-ray tube
(Continued)

support system to move the X-ray tube to perform a first alignment of the X-ray tube with respect to the X-ray detector. After the first alignment, the controller is configured to trigger the optical camera to acquire an image to localize the X-ray detector so as to provide second position information of the X-ray detector, and to generate, based on the second position information of the X-ray detector, a second control signal that is usable for controlling the X-ray tube support system to move the X-ray tube to perform a second alignment of the X-ray tube with respect to the X-ray detector.

14 Claims, 5 Drawing Sheets

(58) Field of Classification Search
CPC .... A61B 1/05; A61B 1/06; A61B 1/04; A61B 6/04; A61B 6/0407; A61B 6/0492; A61B 6/4007; A61B 6/4014; A61B 6/4405; A61B 6/4429; A61B 6/4435; A61B 6/4441; A61B 6/4452; A61B 6/4458; A61B 6/547; A61B 6/587; A61B 6/588; A61B 2034/2055; A61B 2034/2051; A61N 5/1048; A61N 2005/1052; A61N 2005/105; A61N 2005/1054
See application file for complete search history.

(56) References Cited

U.S. PATENT DOCUMENTS

| | | |
|---|---|---|
| 2013/0182829 A1 | 7/2013 | Nguyen |
| 2014/0341356 A1 | 11/2014 | Kurze |
| 2015/0223764 A1 | 8/2015 | Kwak |
| 2016/0174918 A1 | 6/2016 | Wang |
| 2017/0135667 A1 | 5/2017 | Becker |
| 2019/0069864 A1 | 3/2019 | Tkaczyk |
| 2020/0281556 A1 | 9/2020 | Wang |

* cited by examiner

AUTO POSITIONING OF X-RAY TUBE SUPPORT WITH RESPECT TO DETECTOR

FIELD OF THE INVENTION

The present invention generally relates to medical imaging, and in particular relates to a positioning system and a method for controlling an X-ray tube support system to align an X-ray tube with an X-ray detector, to an X-ray imaging system, and to a computer program element.

BACKGROUND OF THE INVENTION

Fully motorized X-ray devices fall under the class of diagnostic X-ray imaging devices. These machines are used to obtain X-ray images of various anatomies to support in arriving at the diagnosis. Systems have an X-ray tube support geometry, which supports the X-ray tube and enables it to position itself as needed in the examination room. X-ray detectors, which quantize the X-ray absorbed to provide a readable image, may be free or mounted on a detector support geometry. Both the X-ray tube and detector support (if present) may have needed mechanisms to ensure proper alignment of the X-ray tube with respect to the X-ray detector. In general there are three types for the alignment including X-ray tube with respect to the X-ray detector in terms of centre and location, angular alignment, and perpendicular source to image distance between both. However, for cases there is no detector support geometry, alignment may have to be done manually which is extremely challenging.

SUMMARY OF THE INVENTION

Thus, there may be a need to facilitate the alignment of an X-ray tube with respect to an X-ray detector e.g., for cases there is no detector support geometry.

The object of the present invention is solved by the subject-matter of the independent claims, wherein further embodiments are incorporated in the dependent claims. It should be noted that the following described aspects of the invention apply also for the positioning system and the method for controlling an X-ray tube support system to align an X-ray tube with an X-ray detector, the X-ray imaging system, and the computer program element According to a first aspect of the present invention, there is provided a positioning system for controlling an X-ray tube support system to align an X-ray tube with an X-ray detector. The positioning system comprises a radio-frequency (RF) based localization system, an optical camera and a controller. The RF-based localization system comprises a first RF device that is attachable to the X-ray detector, and a plurality of second RF devices that are arranged in a known geometric relationship to the X-ray tube and configured to use an RF signal to localize the first RF device so as to provide first position information of the X-ray detector. The controller is configured to generate, based on the first position information of the X-ray detector, a first control signal that is usable for controlling the X-ray tube support system to move the X-ray tube to perform a first alignment of the X-ray tube with respect to the X-ray detector. After the first alignment, the controller is configured to trigger the optical camera to acquire an image to localize the X-ray detector so as to provide second position information of the X-ray detector; and to generate, based on the second position information of the X-ray detector, a second control signal that is usable for controlling the X-ray tube support system to move the X-ray tube to perform a second alignment of the X-ray tube with respect to the X-ray detector.

The inventors of the present invention have found out that the existing automatic alignment method using an optical camera need to have a direct view of landmarks o as a pre-condition. If the optical camera does not have a direct view, alignment may have to be done manually.

In order to facilitate the automatic alignment procedure, the positioning system, the method, the medical imaging system, and the computer program element as described herein perform a two-step alignment procedure. The first alignment is to identify the approximate location and/or orientation of the X-ray detector or detector docking station with the use of a RF-based localization system, like Bluetooth-based localization system, RFID-based localization system, and ultra wideband (UWB)-based localization system. As the first alignment is based on RF signalling, no direct view of the X-ray detector and landmarks on the detector docking station is required.

The second alignment is to identify the accurate location and/or orientation of the X-ray detector or detector docking station with the use of a camera-based localization system. After the source is aligned to X-ray detector approximately, in this position the optical camera will have the view of landmarks on detector or on detector docking station. From this position, using the optical camera it is possible to accurately position the X-ray tube with respect to the X-ray detector. For example, the optical camera may be used to improve the accuracy to few millimetres using image processing from the field of view images.

In this way, an automatic alignment procedure can be achieved even if the X-ray tube supported the X-ray tube support system is located away from the X-ray detector. Thus, manual movements are not needed anymore. In addition, there is no need of performing adjustments relative to each geometries in the field as the alignment is performed automatically in real time. Furthermore, automatic positioning may have a significant impact on the workflow, as there is no need of manually moving the tube support and aligning the same to the X-ray detector, thereby contributing to significant portion of workflow to acquire X-ray images.

The positioning system will be described in detail hereinafter and in particular with respect to the examples shown in FIGS. 2 and 4.

According to an embodiment of the present disclosure, the positioning system further comprises a three-dimensional angle sensor that is attachable to the X-ray detector for three-dimensional angle measurement.

In some examples, the three-dimensional angle sensor may be part of the first RF device.

In some examples, the three-dimensional angle sensor and the first RF device may be two separate devices.

For example, a Gyro sensor may be used for three-dimensional angle measurement.

According to an embodiment of the present disclosure, the first RF device comprises at least one of:
 an RF device that is removably attachable to the X-ray detector or an external handle of the X-ray detector;
 an RF device that is an integrated part of the X-ray detector; or
 an RF device that is an integrated part of an external handle of the X-ray detector.

In some examples, the first RF device may be powered by the X-ray detector.

In some examples, the first RF device may be battery-powered.

Figure 3A:
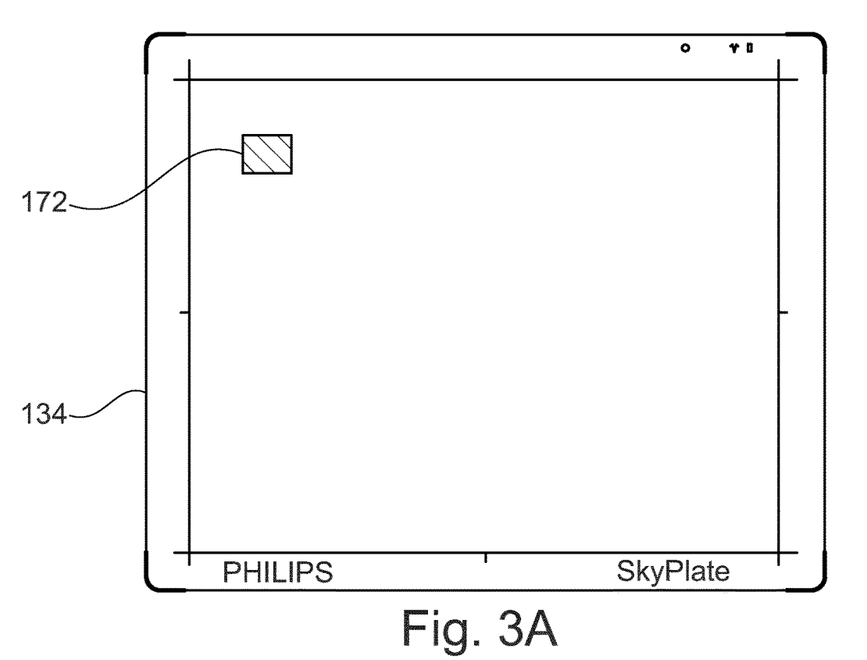
FIG. 3A illustrates an exemplary portable X-ray detector.
Figure 3B:
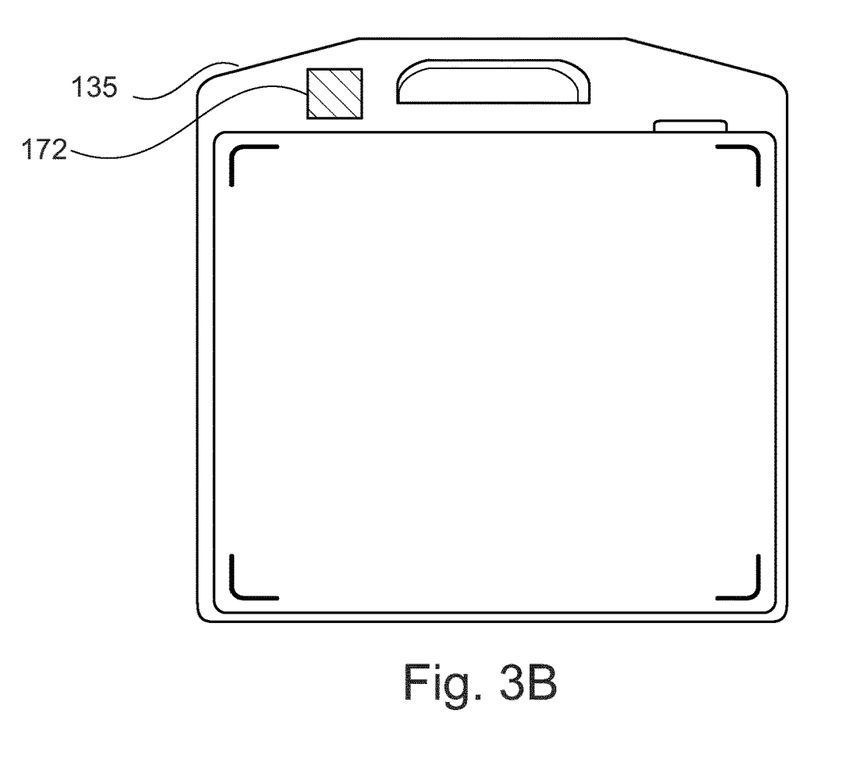
FIG. 3B illustrates an exemplary portable X-ray detector handle.

This will be described in detail hereinafter and in particular with respect to the examples shown in FIGS. 3A and 3B.

According to an embodiment of the present disclosure, the plurality of second RF devices are arranged on the X-ray tube support system.

The location of the plurality of second RF devices may be pre-configured with respect to the X-ray tube support system and only the location of the X-ray tube support system with respect to a room layout has to be calibrated during installation.

In some examples, the second RF devices may be removably attached to the X-ray tube support system.

In some examples, the second RF devices may be integrated with the X-ray tube support system.

In some examples, the second RF devices may be powered by the X-ray tube support system.

In some examples, the second RF devices may be battery powered.

This will be described in detail hereinafter and in particular with respect to the example shown in FIG. 2.

According to an embodiment of the present invention, at least one of the plurality of second RF devices is configured to be interfaced with the X-ray tube support system to with a communication protocol.

For example, the at least one of the plurality of second RF devices may be interfaced with the X-ray tube support system to transmit the collected sensor data to e.g., a system controller.

This will be described in detail hereinafter and in particular with respect to the example shown in FIG. 2.

According to an embodiment of the present disclosure, the RF-based localization system comprise a plurality of ultra-wide band (UWB) devices.

UWB devices are used to locate the detector position in a three-dimensional space. This may be achieved by using one UWB transmitter positioned on the X-ray detector and three or more other UWB receivers positioned on the X-ray tube support system. In some other examples, one UWB receiver may be positioned on the X-ray detector and three or more other UWB receivers may be positioned on the X-ray tube support system.

Various geometric methods may be used for estimation of the position of the X-ray detector. Examples of the geometric methods may include, but are not limited to, trilateration, triangulation, and multilateration.

According to an embodiment of the present disclosure, the first RF device comprises a UWB transmitter.

According to an embodiment of the present disclosure, the plurality of second RF devices comprises at least three UWB receivers.

According to an embodiment of the present invention, there is provided an X-ray detector. The X-ray detector comprises an RF device for location tracking.

The RF device may be part of the X-ray detector or on the external handle of the X-ray detector. An example of the X-ray detectors is illustrated in FIG. 3A. An example of the external handle of the X-ray detector is illustrated in FIG. 3B.

According to an embodiment of the present disclosure, the RF device is an UWB device.

According to an embodiment of the present disclosure, the X-ray detector is a portable X-ray detector.

According to a second aspect of the present invention, there is provided an X-ray imaging system. The X-ray imaging system comprises an X-ray tube configured to emit an X-ray beam and an X-ray tube support system configured to support the X-ray tube. The X-ray imaging system further comprises a positioning system according to the first aspect and any associated example for controlling the X-ray tube support system to align the X-ray tube with an X-ray detector.

In some examples, the X-ray tube support system may be a ceiling support system.

In some examples, the X-ray tube support system may be a floor-to-ceiling support system.

In some examples, the X-ray tube support system may be a mobile digital radiography system.

This will be described in detail hereinafter and in particular with respect to the example shown in FIGS. 2 and 4.

According to a fourth aspect of the present invention, there is provided a method for controlling an X-ray tube support system to align an X-ray tube with an X-ray detector, the method comprises:

obtaining first position information of the X-ray detector utilizing a radio frequency, RF, based localization system, wherein the RF-based localization system comprises a first RF device that is attachable to the X-ray detector, and a plurality of second RF devices that are arranged in a known geometric relationship to the X-ray tube and configured to localize the first RF device using an RF signal;

generating, based on the first position information of the X-ray detector, a first control signal that is usable for controlling the X-ray tube support system to move the X-ray tube to perform a first alignment of the X-ray tube with respect to the X-ray detector;

triggering, after the first alignment, an optical camera to acquire an image to localize the X-ray detector to provide second position information of the X-ray detector; and generating a second control signal that is usable for controlling the X-ray tube support system to move the X-ray tube to perform a second alignment of the X-ray tube with respect to the X-ray detector.

This will be described in detail hereinafter and in particular with respect to the example shown in FIG. 5.

According to a further aspect of the present invention, there is provided a computer program product comprising instructions to cause the positioning system of the first aspect and any associated example to execute the steps of the method of the fourth aspect.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

These and other aspects of the invention will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

While the invention has been illustrated and described in detail in the drawings and following description, such illustration and description are to be considered illustrative or exemplary and not restrictive: the invention is not limited to the disclosed embodiments.

For examples, although this application describes the present invention in medical imaging applications in which the images are produced using X-radiation, it will be appreciated that the present invention may also be advantageously used in applications in which images are obtained using any suitable type of penetrating radiation, or any other particle, wave, or field phenomenon. For example, although this application describes a ceiling mounted digital X-ray system for the implementation of the present approach by way of example, it will be appreciated that the described positioning system is also applicable for other types of X-ray tube support system, such as floor-to-ceiling support system, mobile digital radiography system, etc.

Figure 1:
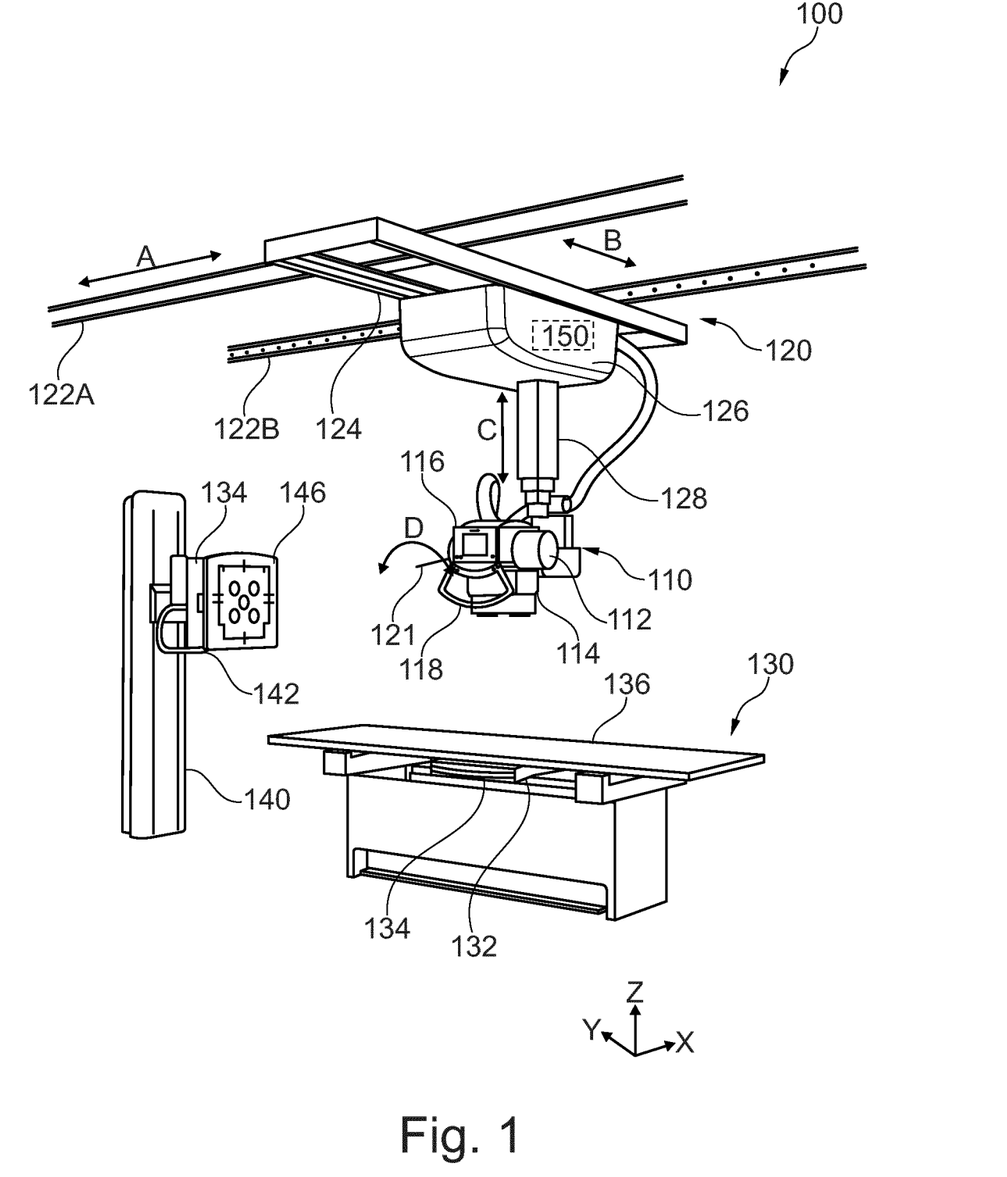
FIG. 1 illustrates an exemplary medical imaging system.

FIG. 1 schematically illustrates a medical imaging system 100 that may be suitable for implementation of the present approach. In the illustrated example, the medical imaging system 100 is a ceiling mounted digital X-ray system.

In the illustrated example, the medical imaging system 100 comprises an X-ray tube head 110 supported from the ceiling (not shown) by an X-ray tube support system 120, a floor mounted examination table 130 for supporting a patient (not shown) with a defined docking compartment 132 in which a portable X-ray detector 134 may be positioned during imaging, and a vertical stand 140 with a defined docking compartment 142 in which a portable X-ray detector 134 may be positioned during imaging. Although not shown, it will be appreciated that the portable X-ray detector 134 may be used for free exams, e.g., on a patient-supporting surface 136 of the floor mounted examination table 130. An example of the portable X-ray detectors 134 is shown in FIG. 3A.

The X-ray tube support system 120 supports the X-ray tube head 110 and provides translational movement of the X-ray tube head 110 in a longitudinal direction (X) shown by arrow A, a transverse (Y) direction shown by arrow B, and a vertical direction (Z) shown by arrow C.

Two spaced parallel support rails 122A and 122B may extend longitudinally along the ceiling (not shown) and are attached thereto by a plurality of fastening means (not shown). A bridge 124 is supported by the support rails 122A and 122B, which also permits longitudinal movement of the bridge 124 and everything it supports, as indicated by the arrow A. The bridge 124 can support a transverse carriage 126 and permit transverse movement of the bridge, as shown by the arrow B. The transverse carriage 126 supports the X-ray tube head 110 by means of a telescoping tube assembly 128 which effectively functions as a vertically oriented linear bearing. The telescoping tube assembly 128 may be formed from a plurality of nested tubular structural members having bearings to allow longitudinal slidable movement therebetween. Thus, the transverse carriage 126 and telescoping tube assembly 128 permit vertical movement of the X-ray tube head 110, as shown by the arrow C.

Movements along directions A and C may be powered by a longitudinal drive 152 (shown in FIG. 4) and a vertical drive 154 (shown in FIG. G. 4) respectively. The longitudinal drive 152 and the vertical drive 154 may be controlled by a system controller 150, which may be housed in the transverse carriage 126. Movements along directions A, B, and C may also be performed manually by the operator.

In the illustrated example, the X-ray tube head 110 may comprise an X-ray tube assembly 112, an X-ray collimator 114, a control panel 116, and control handles 118 for use by the operator in selecting the position of the X-ray tube head 110. Information obtained from control panel 116 may be communicated to the system controller 150, which produces control signals to longitudinal and vertical drives to move the X-ray tube head 110 in the desired direction. The X-ray tube head 110 is mounted on the telescoping tube assembly 128 for rotation about a transverse axis 121, as shown by the arrow D. This may be powered by an X-ray tube head rotational drive 156 (shown in FIG. 4).

Rotation of the X-ray tube head 110 allows the X-ray beam to be directed at various desired angles, such as toward the table 130 or toward the vertical stand 140. The X-ray tube head rotational drive 156 may be controlled by the system controller 150.

Thus, the X-ray tube support system 110, its associated longitudinal and vertical drives 152 and 154, and the X-ray tube head rotational drive 156, cooperate to allow the system controller 150 to direct the X-ray tube head 110 to an arbitrary position on a reference plane is parallel to the X-Z plane, and to point the emitted X-ray beam at an arbitrary angle along the reference plane. It is believed that providing three degrees of freedom for the position of the focal spot and the angular direction of the emitted X-ray beam, under control of the system controller 150, is sufficient for performing examinations using a variety of desirable radiographic, fluoroscopic, and tomographic imaging modes. However, a skilled artisan will appreciate that this embodiment may be easily modified to incorporate additional degrees of freedom if additional imaging modes are desired.

In general there are three types of alignment needed for tube with respect to detector in terms of centre/location, three-axis angular, and source to image distance. Current design solutions achieve angular alignment using Gyro sensor feedback from the detector, which is applicable for cases of detector with free and detector support. Both centre/location and distance alignment are only possible via adjustment during system installation in the field only in cases with detector support geometry. In case of free detector, radiographer has to do both these alignment as per his/her judgement.

In order to facilitate the automatic alignment procedure to improve the workflow, a positioning system 160 is provided for controlling the X-ray tube support system 120 to align an X-ray tube 112 with an X-ray detector 134. With the positioning system, an automatic alignment procedure can be achieved even if the X-ray tube supported the X-ray tube support system is located away from the X-ray detector. Thus, manual movements are not needed anymore. In addition, there is no need of performing adjustments relative to each geometries in the field as the alignment is performed automatically in real time. Furthermore, automatic positioning may have a significant impact on the workflow, as there is no need of manually moving the tube support and aligning the same to the X-ray detector, thereby contributing to significant portion of workflow to acquire X-ray images.

Figure 2:
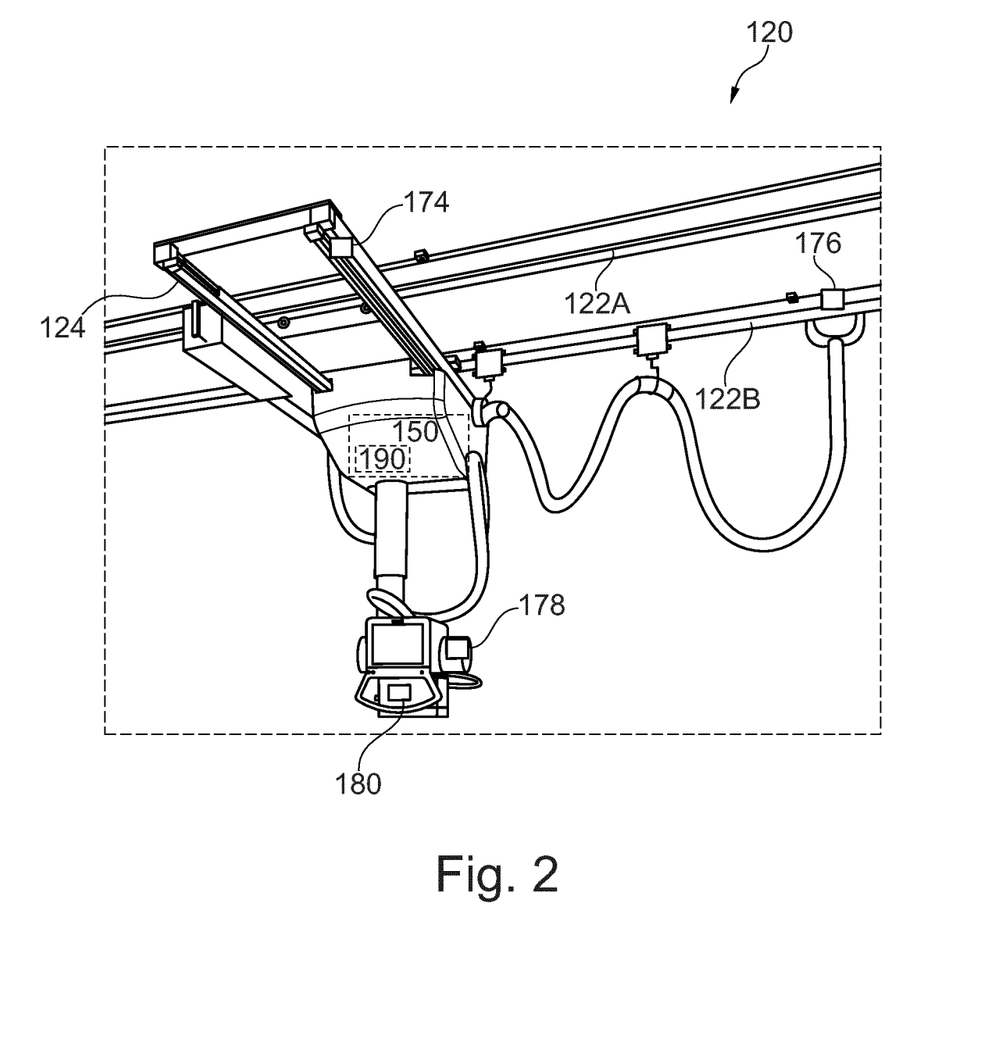
FIG. 2 illustrates an exemplary positioning system.

FIG. 2 illustrates an exemplary positioning system 160. The exemplary positioning system comprises an RF-based localization system 170, an optical camera 180, and a controller 190.

The RF-based localization system 170 comprises a first RF device 172 that is attachable to the X-ray detector 134. An example of the X-ray detector 134 is illustrated in FIG. 3A. In some examples, as illustrated in FIG. 3A, the first RF device 172 may be removably attached or integrated with the portable X-ray detector 134. In some other examples, as illustrated in FIG. 3B, the first RF device 172 may be removably attached or integrated with an external detector handle 135 of the portable X-ray detector.

The RF-based localization system 170 further comprises a plurality of second RF devices that are arranged in a known geometric relationship to the X-ray tube. For example, as shown in FIG. 2, the plurality of second RF devices may comprise three RF devices, namely RF device 174. RF device 176, and RF device 178. In some other examples (not shown), the plurality of second RF devices may comprise four, five, six, or more RF devices. The plurality of second RF devices, such as RF devices 174, 176, and 178 illustrated in FIG. 2, may be removably attached or integrated with the X-ray tube support system 120. The location of the three RF devices 172, 174, and 178 is flexible, but in general for better accuracies of location each of the three RF devices 172, 174, and 178 should be farther away as much as possible with respect to another. The location of these RF devices may be pre-configured with respect to the X-ray tube support system 120 and only the location of the X-ray tube support system 120 with respect to the room layout has to be calibrated during installation. For example, as illustrated in FIG. 2, the RF device 174 may be removably attached or integrated on the bridge 124. The RF device 176 may be removably attached or integrated on the support rail 122B. The RF device 178 may be removably attached or integrated on the X-ray tube head 110. During movement of the ceiling suspension some of the RF devices 174, 176, and 178 may be moved from their initial position but that change can be accurately estimated by using internal position sensor feedback in each axes of the X-ray tube support system 120. At last as one of the second RF devices 174, 176, and 178 may act as a master which collects data from other RF devices to determine the location of first RF device 172 on the X-ray detector. This master RF device(s) may be interfaced to X-ray tube support system 120 with a needed communication protocol to provide the sensor data to the controller 190.

The plurality of second RF devices, such as RF devices 174, 176, and 178, are configured to use an RF signal to localize the first RF device 172 so as to provide first position information of the X-ray detector 112. In some examples, the first RF device 172 on the X-ray detector may be an RF transmitter, and the plurality of second RF devices, such as RF devices 174, 176, and 178 on the X-ray tube support system 120, may be RF receivers. In some other examples, the first RF device 172 on the X-ray detector may be an RF receiver, and the plurality of second RF devices, such as RF devices 174, 176, and 178 on the X-ray tube support system 120, may be RF transmitters.

Various geometric methods may be used for estimation of the position of the first RF device 120. Examples of the geometric methods may include, but are not limited to, trilateration, triangulation, and multilateration. The trilateration method is based on range measurements, from the unknown location of the first RF device (e.g., RF device 172) to other anchor points (e.g., RF devices 174, 176, and 178) with known coordinates. The distances (also referred to as range) may be estimated by measuring different RF parameters, such as received power or radio signal propagation time. i.e., time of flight. The triangulation method for location method is similar to the trilateration. The unknown location of the first RF device (e.g., RF device 172) is estimated by measuring the angles between the anchor points (e.g., RF devices 174, 176, and 178) and the point (e.g., RF device 172) with unknown location. Multilateration may be used in systems where only information for the difference of the distances from the unknown location of the first RF device (e.g., RF device 172) to the anchor nodes (e.g., RF devices 174, 176, and 178) can be measured. The node (e.g., RF device 172) residing on an unknown location measures the time difference between the arrival of the signals from the anchor nodes (e.g., RF devices 174, 176, and 178).

The RF-based localization system 160 may be a Bluetooth Low Energy (BLE)-based localization system. Wi-Fi-based localization system. RFID-based localization system. UWB-based localization system, or any combination thereof. Take the UWB-based localization system for example, the first RF device 172 as shown in FIG. 2 may be a UWB transmitter, and the plurality of second RF devices, such as RF devices 174, 176, and 178 as shown in FIG. 2, may be UWB receivers. The UWB-based localization system may achieve an accuracy within a few centimetres with reasonably positioned RF devices. As the accuracy is within few centimetres with UWB sensors, detector will be within the field of view of the optical camera 120.

In some examples, the positioning system may comprise a three-dimensional angle sensor 173 (see FIG. 4) that is attachable to the X-ray detector for three-dimensional angle measurement. In some examples, the three-dimensional angle sensor may be part of the first RF device. In some examples, the three-dimensional angle sensor and the first RF device may be two separate devices. For example, a Gyro inertial measurement unit (IMU) sensors integrated with the first RF device 172 may provide information needed to achieve angular alignment of X-ray tube with respect to the X-ray detector.

The optical camera 120 is used to improve the accuracy of alignment to few millimetres e.g., using image processing from the field of view images. The optical camera 120 may be positioned in the collimator 114 or at any other suitable location on the X-ray tube head 110 for a view of the X-ray detector or a region (e.g., table surface) that contains the X-ray detector. The term "image" or "image data" as used herein is to be understood broadly in the present case and comprises any data or electromagnetic radiant imagery that may be obtained or generated by the optical camera 120. Although only a single optical camera 120 is illustrated in FIG. 2 by way of example, it will be appreciated that a plurality of optical cameras or a plurality of image sensors may be deployed. Image data are not limited to the visible spectral range and to two dimensionalities. Examples of the image acquired by the optical camera may include, but are not limited to, grayscale images, near infrared (NIR) images, RGB images, multispectral images, and hyperspectral images. The frame rate of the camera may be in the range of 0.3 Hz to 48 Hz, but is not limited thereto. The optical camera may be pre-configured to recognize the X-ray detector and its centre location using patterns or unique identifiers. This optical camera may be integrated to the X-ray tube support system 120, which comprises the system controller 150 to perform the needed image processing process to adjust and align the X-ray tube with respect to the X-ray detector.

The controller 190 may comprise various physical and/or logical components for communicating and manipulating information, which may be implemented as hardware components (e.g. computing devices, processors, logic devices), executable computer program instructions (e.g. firmware, software) to be executed by various hardware components, or any combination thereof, as desired for a given set of design parameters or performance constraints. In some implementations, the controller 190 may comprise one or more microprocessors or computer processors, which execute appropriate software. The software may have been downloaded and/or stored in a corresponding memory, e.g. a volatile memory such as RAM or a non-volatile memory such as flash. The software may comprise instructions configuring the one or more processors to perform the functions described herein. It is noted that the controller 190 may be implemented with or without employing a processor, and also may be implemented as a combination of dedicated hardware to perform some functions and a processor (e.g. one or more programmed microprocessors and associated circuitry) to perform other functions. For example, the controller 190 may be implemented in the device or apparatus in the form of programmable logic, e.g. as a Field-Programmable Gate Array (FPGA). In the example of FIG. 2, the controller 190 is embodied in the system controller 150. In some other examples (not shown), the controller 190 may be embodied as, or in, other devices, e.g., a workstation.

The controller 190 may execute instructions to perform the method described herein, which will be explained in detail with respect to the example shown in FIGS. 4 and 5.

Figure 4:
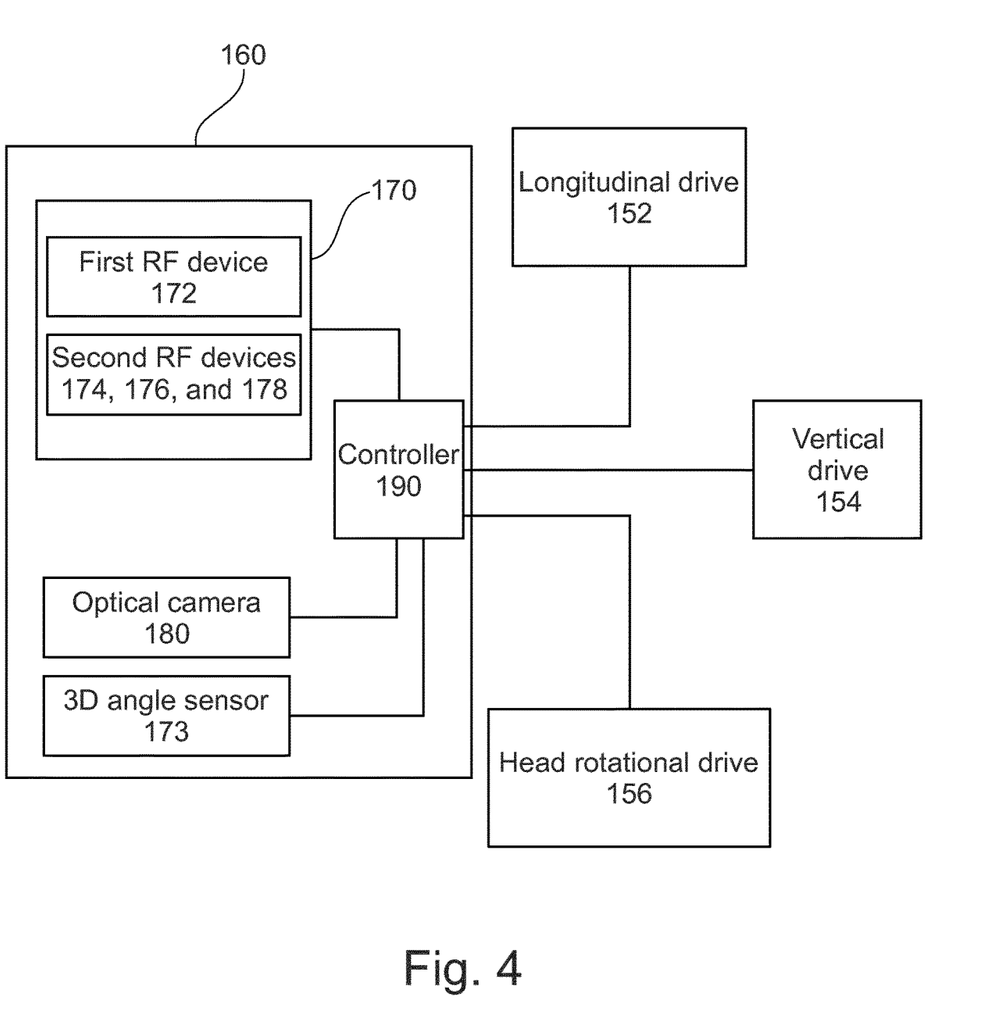
FIG. 4 illustrates the positioning system and the relationship with some components of the X-ray tube support system.

FIG. 4 diagrammatically illustrates the positioning system 160 and the relationship with some components of the X-ray tube support system. In the illustrated example, the controller 190, in accordance with the present approach, may receive inputs from the RF-based localization system 170, the optical camera 180, and the optional three-dimensional angle sensor 173 of the positioning system 160 to facilitate determination of a detector position and/or orientation relative to the X-ray tube 112. In addition, as discussed herein, based upon the relative position of the source and the detector, the controller 190 may control or adjust the alignment of the X-ray tube 112 with respect to the X-ray detector, e.g., detector 134. For example, movements of the X-ray tube along directions A and C may be powered by the longitudinal drive 152 and a vertical drive 154 respectively. The rotation of the X-ray tube head may be powered by the head rotational drive 156.

Figure 5:
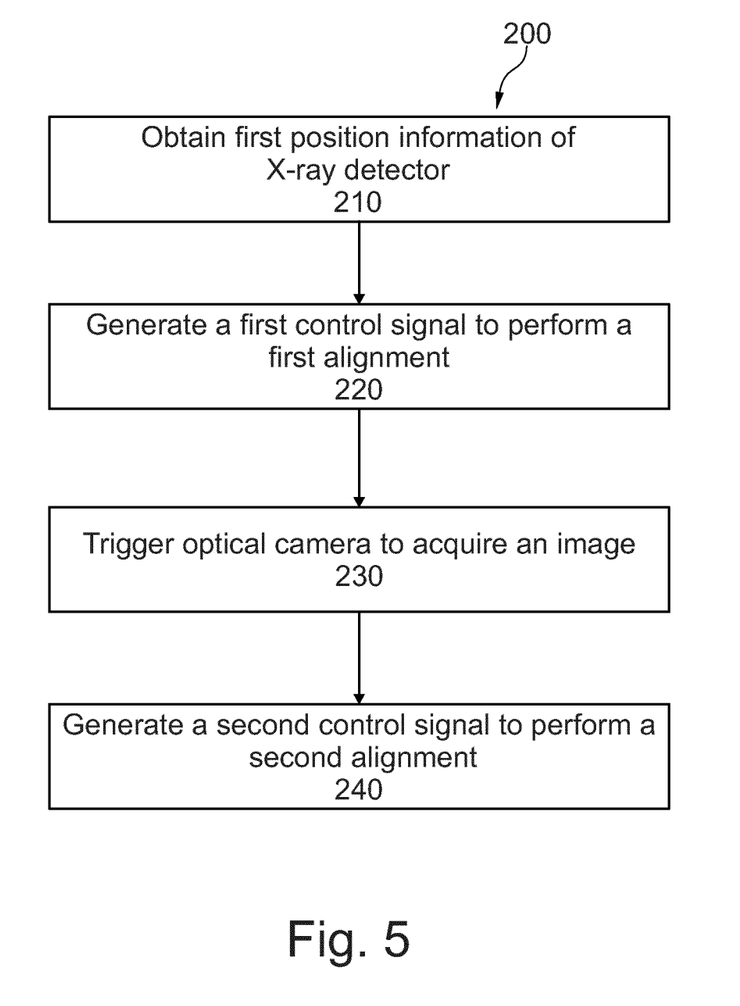
FIG. 5 illustrates a flowchart describing a method for controlling an X-ray tube support system to align an X-ray tube with an X-ray detector.

FIG. 5 illustrates a flowchart describing a method 200 for controlling an X-ray tube support system to align an X-ray tube with an X-ray detector. The method 200 will be described in connection with the system shown in FIGS. 2 and 4.

At block 210, an RF-based localization system 160 obtains first position information of the X-ray detector e.g., a portable X-ray detector 134. The first position information comprises approximate position information which might not be accurate enough, e.g., with an accuracy of more than 1 to 2 centimetre depending on the RF localization technologies. The RF-based localization system 160 comprises a first RF device, e.g., RF device 172 illustrated in FIGS. 3A and 3B, which is attachable to the X-ray detector 134 or to the X-ray detector handle 135. The first RF device 172 may be part of the X-ray detector itself or on the external handle of the X-ray detector. Alternatively, the first RF device 172 may be removably attached to the X-ray detector or to the external handle of the X-ray detector. The RF-based localization system 160 further comprises a plurality of second RF devices, such as RF devices 174, 176, and 178 as shown in FIG. 2, which are arranged in a known geometric relationship to the X-ray tube and configured to localize the first RF device using an RF signal.

In some examples, the first RF device may be an RF transmitter, and the second RF devices may be RF receivers. In some examples, the RF receiver and transmitter combination can be vice-versa. In other words, only if X-ray tube support system has RF receivers then the detector should have a transmitter, and if detector has an RF receiver then tube support should have RF transmitters.

The RF-based localization system may be a Bluetooth/BLE, Wi-Fi, RF identification (RFID), a UWB-based localization system, or any combination thereof. Taking the UWB-based localization system for example, the first RF device 172 as shown in FIG. 2 may be a UWB transmitter, and the plurality of second RF devices, such as devices 174, 176, and 178 as shown in FIG. 2, may be UWB receivers. The three UWB receivers 174, 176, and 178 positioned on the X-ray tube support system may receive the signal from the UWB transmitter 172 from the X-ray detector and the Time Difference on Arrival (TDOA) approach may be utilized to look at the difference in arrival time of the signal between each receiver 174, 176, and 178 to localize the transmitter position.

At block 220, based on the first position information of the X-ray detector, the controller 190 generates a first control signal that is usable for controlling the X-ray tube support system to move the X-ray tube to perform a first alignment of the X-ray tube with respect to the X-ray detector. For example, movements of the X-ray tube along directions A and C may be powered by the longitudinal drive 152 and a vertical drive 154 respectively. The rotation of the X-ray tube head may be powered by the head rotational drive 156. As the RF-based localization system may have an accuracy within a few centimetres, the X-ray detector will be within the field of view of the optical camera 180 after the first alignment.

At block 230, after the first alignment, the controller 190 triggers the optical camera 180 to acquire an image to localize the X-ray detector to provide second position information of the X-ray detector. The second position information comprises the fine position information, i.e., accurate position information. The portable X-ray detector 134 may be used for free exams or inserted in a defined docking compartment in the floor mounted examination table 130 or in the vertical stand 140. In some examples, if the portable X-ray detector 134 is inserted in the defined docking compartment in the floor mounted examination table 130, the controller 190 may analyse an image of one or more landmarks provided on the patient-supporting surface 136 of the floor mounted examination table 130 to localize the X-ray detector. In some examples, if the portable X-ray detector 134 is inserted into the defined docking compartment in the vertical stand 140, the controller 134 may analyse the marking or pattern on a surface 146 to localize the X-ray detector. In some examples, if the portable X-ray detector 134 is used for free exams e.g., positioned on the patient-supporting surface 136 of the floor mounted examination table 130, the controller 190 may analyse an image of the X-ray detector to localize the X-ray detector. In this way, it is possible to improve the accuracy of locating the X-ray detector to a millimetre range or less than a millimetre range.

At block 240, based on the first position information of the X-ray detector, the controller 190 generates a second control signal that is usable for controlling the X-ray tube support system to move the X-ray tube to perform a second alignment of the X-ray tube with respect to the X-ray detector. In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measured cannot be used to advantage. Any reference signs in the claims should not be construed as limiting the scope.

The invention claimed is:

1. A positioning system for controlling an X-ray tube support system to align an X-ray tube with an X-ray detector, the system comprising:
   a radio frequency, RF, based localization system;
   an optical camera; and
   a controller;
   wherein the RF-based localization system comprises:
      a first RF device that is attachable to the X-ray detector, and
      a plurality of second RF devices that are arranged in a known geometric relationship to the X-ray tube and configured to use an RF signal to localize the first RF device so as to provide first position information of the X-ray detector;
   wherein the controller is configured to generate, based on the first position information of the X-ray detector, a first control signal that is usable for controlling the X-ray tube support system to move the X-ray tube to perform a first alignment of the X-ray tube with respect to the X-ray detector; and
   wherein after the first alignment, the controller is configured to trigger the optical camera to acquire an image to localize the X-ray detector so as to provide second position information of the X-ray detector, and to generate, based on the second position information of the X-ray detector, a second control signal that is usable for controlling the X-ray tube support system to move the X-ray tube to perform a second alignment of the X-ray tube with respect to the X-ray detector.

2. The positioning system according to claim 1, further comprising:
   a three-dimensional angle sensor that is attachable to the X-ray detector for three-dimensional angle measurement.

3. The positioning system according to claim 1, wherein the first RF device comprises at least one of:
   an RF device that is removably attachable to the X-ray detector or an external handle of the X-ray detector;
   an RF device that is an integrated part of the X-ray detector; or
   an RF device that is an integrated part of an external handle of the X-ray detector.

4. The positioning system according to claim 1, wherein the plurality of second RF devices are arranged on the X-ray tube support system.

5. The positioning system according to claim 4, wherein at least one of the plurality of second RF devices is configured to be interfaced with the X-ray tube support system with a communication protocol.

6. The positioning system according to claim 1, wherein the RF-based localization system comprise a plurality of ultra-wide band, UWB, devices.

7. The positioning system according to claim 6, wherein the first RF device comprises a UWB transmitter.

8. The positioning system according to claim 7, wherein the UWB transmitter comprises the three-dimensional angle sensor.

9. The positioning system according to claim 5, wherein the plurality of second RF devices comprises at least three UWB receivers.

10. An X-ray imaging system, comprising:
    an X-ray tube configured to emit an X-ray beam;
    an X-ray tube support system configured to support the X-ray tube;
    a positioning system according to claim 1 for controlling the X-ray tube support system to align the X-ray tube with an X-ray detector.

11. The X-ray imaging system according to claim 10, wherein the X-ray detector comprises a radio frequency, RF, device for location tracking.

12. The X-ray imaging system according to claim 11, wherein the RF device is an ultra-wide band, UWB, device.

13. The X-ray imaging system according to claim 11, wherein the X-ray detector is a portable X-ray detector.

14. A method for controlling an X-ray tube support system to align an X-ray tube with an X-ray detector, the method comprises:
- obtaining first position information of the X-ray detector utilizing a radio frequency, RF, based localization system, wherein the RF-based localization system comprises a first RF device that is attachable to the X-ray detector, and a plurality of second RF devices that are arranged in a known geometric relationship to the X-ray tube and configured to localize the first RF device using an RF signal;
- generating, by a controller based on the first position information of the X-ray detector, a first control signal that is usable for controlling the X-ray tube support system to move the X-ray tube to perform a first alignment of the X-ray tube with respect to the X-ray detector;
- triggering, by the controller after the first alignment, an optical camera to acquire an image to localize the X-ray detector to provide second position information of the X-ray detector; and
- generating, by the controller based on the second position information of the X-ray detector, a second control signal that is usable for controlling the X-ray tube support system to move the X-ray tube to perform a second alignment of the X-ray tube with respect to the X-ray detector.

* * * * *